United States Patent [19]
Ruckenstein et al.

[11] Patent Number: 5,993,661
[45] Date of Patent: Nov. 30, 1999

[54] MACROPOROUS OR MICROPOROUS FILTRATION MEMBRANE, METHOD OF PREPARATION AND USE

[75] Inventors: Eli Ruckenstein, Amherst; Xianfang Zang, Buffalo, both of N.Y.

[73] Assignee: The Research Foundation of State University of New York, Amherst, N.Y.

[21] Appl. No.: 08/834,644

[22] Filed: Apr. 14, 1997

[51] Int. Cl.⁶ .......................... B01D 61/00; B01D 39/00
[52] U.S. Cl. .................. 210/651; 210/636; 210/500.29; 210/500.42; 210/500.23; 210/490; 210/231; 264/41; 264/200
[58] Field of Search .................. 210/500.29, 500.36, 210/500.42, 636, 500.23, 651, 490, 231; 264/41, 200

[56] References Cited

U.S. PATENT DOCUMENTS

| | | | |
|---|---|---|---|
| 3,546,209 | 12/1970 | Lipps, Jr. .......................... | 210/500.29 |
| 4,220,477 | 9/1980 | Kesting ...................... | 264/41 |
| 4,279,752 | 7/1981 | Sueoka et al. ............... | 264/49 |
| 4,882,060 | 11/1989 | Schmer ............................. | 210/500.29 |
| 4,983,304 | 1/1991 | Tsugita et al. .......................... | 210/640 |
| 5,006,255 | 4/1991 | Uragami . | |
| 5,116,747 | 5/1992 | Moo-Young et al. . | |
| 5,136,032 | 8/1992 | Nagamatsu et al. .................... | 210/654 |
| 5,155,144 | 10/1992 | Manganaro et al. ...................... | 521/61 |
| 5,427,684 | 6/1995 | Diamantoglou et al. .......... | 210/500.29 |
| 5,723,601 | 3/1998 | Larsson .................................. | 536/165 |
| 5,760,097 | 6/1998 | Li et al. ................................... | 521/61 |

FOREIGN PATENT DOCUMENTS 0204211  12/1982  Japan ............................... 210/500.29

OTHER PUBLICATIONS

T. Uragami, Y. Ohsumi and M. Sugihara, (1981), Studies on synthesis and permeability of special polymer membranes; Polymer, vol. 22, pp. 1155–1156.

X. Zeng and E. Ruckenstein, (1996), Supported chitosan–dye affinity membranes and their protein absorption; J. Membrane Sci., vol. 117, pp. 271–178.

T. Yang and R.R. Zall, (1984), Chitosan Membranes for Reverse Osmosis Application; J. Food Science vol. 49, pp. 91–93.

M. Goto, A.A. Shiosaki and T. Hirose, (1994), Separation of Water/Ethanol Vapor Mixtures through chitosan and cross–linked chitosan membranes; Separation Science and Tech., vol. 29, pp. 1915–1923.

M. Beppu, T. Baba and C. Kamizawa, (1993), Effect of organic solvents as gelating agents on performance of chitosan membranes for ultrafiltration; Kobunshi Ronbunshu, vol. 50, pp. 35–40.

X. Zheng, C. Mingde, Z. Xurong and S. Jun, (1993), Pervaporation separation of ethanol–water mixture using crosslinked chitosan/PAN membrane; Membrane Sci. & Technol., vol. 13, pp. 29–32.

C.J. Brine and P.R. Austin, (1975), Renatured chitin fibrils, films and filaments, ACS Symposium series vol. 18, pp. 505–518.

F.A. Rutherford and P.A. Austin, (1977), Marine Chitin Properties and Solvents, Proc. First International Conference on Chitin and Chitosan, pp. 182–192.

Primary Examiner—Ana Fortuna
Attorney, Agent, or Firm—Hodgson, Russ, Andrews, Woods & Goodyear LLP

[57] ABSTRACT

This invention relates to a microporous or macroporous affinity filtration membrane wherein the matrix is composed of chitosan or chitin and the pores are made by dissolution of porogen during the preparation of the membrane. The invention also relates to a method of preparation of the membrane comprising preparing an acidic chitosan solution containing porogen, shaping the suspension into a membrane, and dissolving the porogen by immersing the membrane in an alkaline solution. To prepare chitin membranes, the chitosan membranes are acetylated. The special feature of the membrane is that the pore size can be controlled by varying the size of the porogen. The membranes are suitable for affinity purification of macromolecules.

40 Claims, 8 Drawing Sheets

MACROPOROUS OR MICROPOROUS FILTRATION MEMBRANE, METHOD OF PREPARATION AND USE

BACKGROUND OF THE INVENTION

1. Field of the Invention

The present invention relates to the area of affinity purification of macromolecules. More particularly, the invention provides an affinity membrane, wherein the pore size is based upon the size of the porogen selected, a method for preparation of the membrane, and a method for affinity purification of macromolecules.

2. Description of Related Art

Affinity membrane filtration (AMF) has recently emerged as an alternative to affinity column chromatography. An advantage of AMF is that high flow rates at low pressure drops can be achieved, thereby greatly improving the washing, elution, and regeneration processes, and decreasing the probability of deactivation of the biomolecules by shortening their exposure to an unfavorable medium.

The key to efficient AMF is the preparation of the affinity membranes. In general, two approaches have been employed to prepare affinity membranes. In the most common method, microporous affinity membranes are prepared from polyethylene, polypropylene, nylon, polysulfone, and glass. However, these membranes are usually hydrophobic and relatively inert, and hence require modifications. In addition, some of the membranes may require amplification of the number of active groups. To overcome these drawbacks, a second approach has been employed wherein membranes are prepared that have preincorporated functional groups. However, the problems with this type of membranes include hydrophobicity (poly glycidyl methacrylate-co-ethylene dimethacrylate membrane), brittleness, and solubility in acids (cellulose acetate membrane). Another drawback with both of the above methods is that the pore size of the membrane cannot be easily controlled.

Recently chitosan membranes have been suggested as affinity membranes for immobilization of various macromolecules having affinity for chitosan. Next to cellulose, chitin (poly (N-acetyl-D-glucosamine)), is the most abundant biopolymer. Chitosan, the deacetylated form of chitin, is soluble in dilute aqueous organic acids but is insoluble in alkaline solutions. Chitosan molecules contain a large number of reactive hydroxyl and amine groups, which can easily attach ligands. In view of its hydrophilicity, excellent film-forming ability, good mechanical properties, and high chemical reactivity (containing hydroxyl and amine groups), chitosan can be an excellent candidate for filtration membranes. Moreover, since chitosan has a positive charge due to the presence of —$NH_2$ groups, it can be used to selectively adsorb malignant leukemia cells which carry a higher negative charge on their surface than normal cells. Since chitin contains N-acetyl-D-glucosamine units in its structure which can bind certain molecules, it can be employed for affinity purification without further chemical modification. Other advantages of chitosan and chitin are that they are easily available and inexpensive. Moreover, chitin and crosslinked chitosan are insoluble in both acidic and alkaline media making them suitable as filtration membranes.

In addition to affinity filtration, other uses of chitosan membranes include reverse osmosis (Yang and Zall, 1984 *J. Food Sci.,* vol 49:91–93), pervaporation (Tsugita et al., U.S. Pat. No. 4,983,304; Zeng et al., 1993 *Membr. Sci. Technol.,* vol 13:29–32; Goto et al., 1994 *Sep. Sci. Technol.* vol 29:1915–23), ultrafiltration (Beppu et al., 1993 *Kobunshi Ronbunshu* vol 50:35–40), and affinity filtration (Zeng and Ruckenstein 1996 *J. Membr. Sci.* vol 117:271–278). U.S. Pat. No. 5,116,747 to Moo-Young et al. describes the use of a semi-permeable membrane, formed by chitosan and a water soluble polymer, for immobilization of biologically active material. U.S. Pat. No. 5,006,255 to Uragami describes a selective permeable membrane prepared by cross-linking of chitosan by aldehyde, and used for separation of water-alcohol solution.

Currently, there is no suitable method available for the preparation of microporous or macroporous chitosan membranes wherein the size of the pores can be controlled. The most common method to prepare microporous chitosan membranes is the phase-inversion process, using a large molecular weight organic compound as a porogen. The process involves three steps: (1) casting of a solution of the membrane containing a porogen and partial evaporation of the solvent; (2) sol-gel transformation and generation of pores via the addition of a solvent for the porogen; and (3) heat treatment for stabilizing the pore structure and improving the mechanical properties. This method requires rigorous control of various parameters, particularly the kind and amount of porogen and evaporation conditions (time, humidity and temperature). Generally, the porogens employed in the phase-inversion methods for preparing hydrophobic membranes were organic compounds of low molecular weight such as acetone, dimethyl formamide, dimethyl sulfoxide, benzene, etc. To obtain large pores in chitosan membranes, the relatively large molecule of poly (ethylene glycol), molecular weight 35,000, was used as porogen (Zeng and Ruckenstein, 1996 *J. Membr. Sci.* vol 117:271–278). Although relatively high permeability membranes were obtained, their mechanical properties were not satisfactory, and they had to be placed on another support.

So far, microporous or macroporous chitin membranes have not been available, primarily because no suitable solvent and porogen could be found. A few solvents, such as the mixtures trichloroacetic acid-chloral hydrate-dichloromethane (Brine and Austin, 1975 ACS Symposium Series, Church T. D., Eds., American Chemical Soc., vol 18, p505), dimethylacetamide (DMAc)-LiCl (Rutherford and Austin, 1977 *Proc. of the First International Conf. on Chitin and Chitosan,* Muzzaralli, R. A. A., Priser, E. R., Eds., MIT Sea Grant Program, Cambridge), and N-methyl-2-pyrrolidone-DMAc-LiCl (Uragami et al., 1981 *Polym.,* vol 30:1155–1156) have been tried. However, it was either almost impossible to completely dissolve chitin in these solvents, or required a long time, followed frequently by degradation.

SUMMARY OF THE INVENTION

An object of the present invention is to provide a macroporous or microporous filtration membrane for affinity purification of macromolecules, wherein the matrix comprises chitosan or its acetylated form, chitin, and the size of the pores can be controlled.

Another object of the present invention is to provide a method for the preparation of chitosan or chitin membranes wherein the matrix of the membrane is formed around a porogen of desired size. The porogen particles are then dissolved to form the membrane pores.

A further object of the invention is to provide a method for affinity purification of molecules having an affinity for chitosan or chitin.

DETAILED DESCRIPTION OF THE INVENTION

Figure 1A:
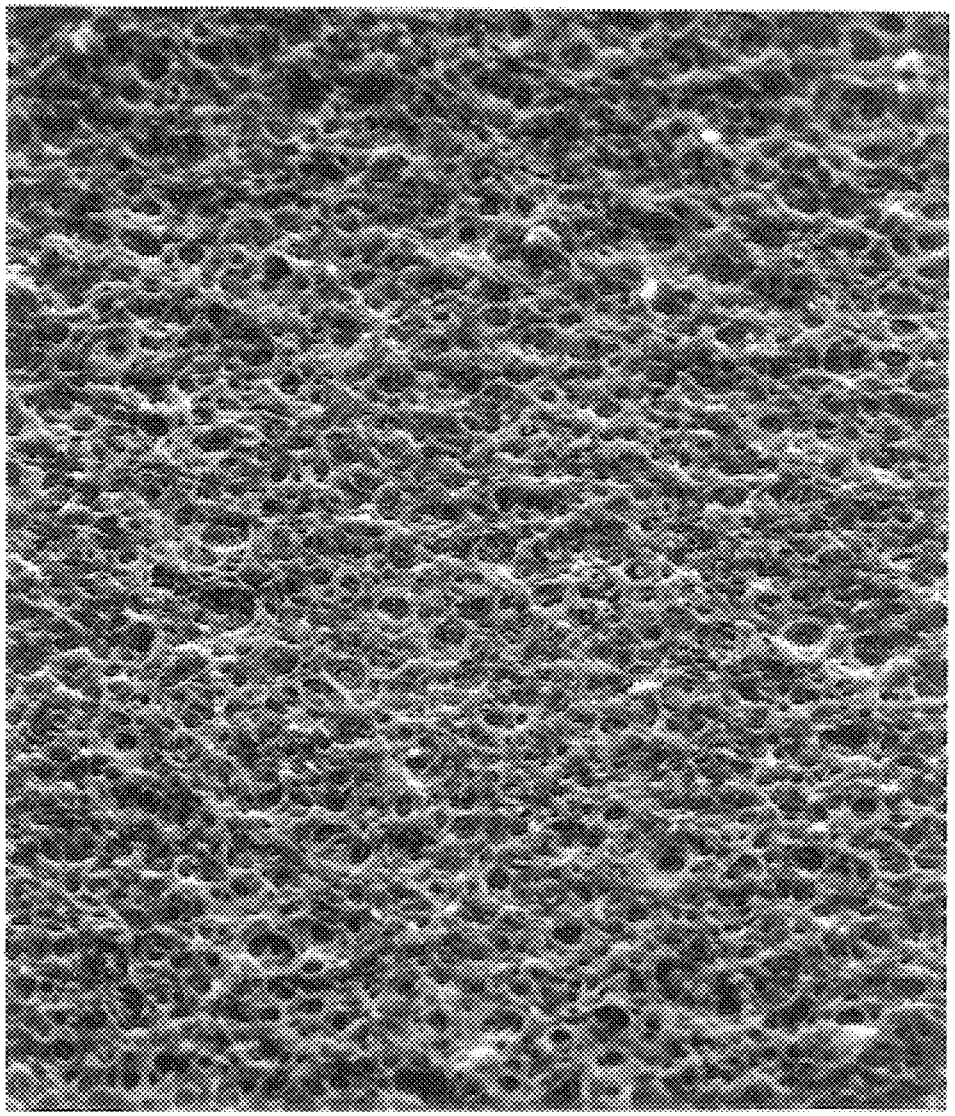
FIG. 1*a* is a scanning electron micrograph showing the morphology of a macroporous chitosan membrane, wherein the weight ratio of silica particles to chitosan is 4:1 and the size of silica particles is 5 μm.

"Macroporous" as used herein means pores having a diameter of at least 1.0 μm.

"Microporous" as used herein means pores having a diameter of from 0.1 μm to about 1.0 μm.

"Membrane" as used herein means a membrane wherein the matrix can be of any shape including, but not limited to, flat surfaces and spheres.

The present invention is concerned with a porous affinity membrane wherein the matrix comprises chitosan or chitin, and wherein the pores are created by dissolution of the porogen. The pores can be in the micro—(diameter 0.1 μm to 1.0 μm) or macro—(diameter greater than 1.0 μm) range depending upon the size of the porogen selected for the preparation of the membranes.

To prepare the membrane of the present invention, commercially available chitosan such as, but not limited to, chitosan of molecular weight about 70,000 to about 2,000,000, can be used. While chitosan of any molecular weight can be used, a preferred embodiment has chitosan of molecular weight between about 400,000 to about 2,000,000.

Any porogen in particulate form that is soluble in basic solutions and insoluble in acidic ones can be used. It is preferable to use an inorganic porogen in order to obtain a dried chitosan membrane rather than a chitosan gel membrane. Suitable porogens include, but are not limited to, silica, aluminum silicate and aluminum oxide.

In one illustrative embodiment, the porogen is silica. Since silica is available in several sizes, a wide range of pore size can be achieved. In a more preferred embodiment, the size of silica particles is from about 15 μm to about 40 μm which results in an average pore size of 19.8 μm for chitosan membranes and 17.9 μm for chitin membranes.

Chitosan membranes are prepared according to the process of the present invention by first preparing a suspension of the porogen particles in an aqueous acidic solution of chitosan. To prepare acidic chitosan solution, organic acids were found to be particularly suitable for this invention. Such acids include, but are not limited to, acetic acid, formic acid, dichloroacetic acid, and trifluoroacetic acid. However, non-organic acids such as, but not limited to, hydrochloric acid, also work well. In a preferred embodiment, the acid is acetic acid. The concentration of chitosan in the aqueous acidic solution is inversely related to its molecular weight. For example, for an average molecular weight of 750,000, the appropriate concentration is around 0.5 wt % to 1.5 wt %. For the lower molecular weight of 70,000 the concentration is around 2 wt % to 6 wt percent.

The acidic chitosan solution containing the porogen is shaped into the desired membrane form. For preparing flat sheets, the suspension is cast on a rimmed glass plate and the solvent is allowed to evaporate. For hollow fibers, the pressurized suspension is extruded through a spinneret into a coagulation bath and for preparing beads, the pressurized suspension is dropped through a nozzle into a coagulation bath. The coagulation bath comprises NaOH. In addition, it may also contain ethanol or methanol.

The porogen particles are easily extracted by exposing the shaped membranes to an alkaline solution. It may be desirable to carry out the treatment with the alkaline solution at a higher temperature so as to accelerate dissolution of silica and generate a porous membrane. In addition, heat treatment also improves the mechanical properties of the membrane. The time of exposure to the alkaline solution is dependent upon the temperature. For example, at 80° C., a 2 hour treatment was found to be adequate, while at room temperature, a 24 hour treatment was necessary. Chitosan is insoluble in alkaline solution and hence is unaffected by this treatment.

Following dissolution of the porogen, the alkaline solution is removed by washing with water and then the membrane is either allowed to dry or can be stored in methanol or ethanol. In a preferred embodiment, the to membrane is treated, before drying, with a plasticizer, which acts as a softening agent. This reduces the shrinkage during drying but has only a minimal effect on the flow rate through the membrane. Such plasticizers include, but are not limited to glycerol, ethylene glycol, propylene glycol, diethylene glycol, triethylene glycol and trimethylene glycol. Glycerol is a particularly suitable plasticizer.

Alternatively, the plasticizer may be included in the chitosan-porogen suspension.

The number of pores in a membrane can be controlled by changing the weight ratio of silica to chitosan. For example, increase of this ratio from 1:1 to 2:1 rapidly increases the flow rate of pure water through the membrane prepared with silica particles in the range 15 μm to 40 μm.

The flow rate increases, however, only slightly for ratios larger than 2:1, because the resultant membrane is more easily compressed at higher pressure drops. Membranes prepared with silica particles of other sizes also display a similar behavior.

In affinity separation processes, the proteins or enzymes adsorbed are often eluted at low pH. To prevent the dissolution of the membranes in acidic solutions, the membrane is treated with a cross-linking agent. Any cross-linking agent that reacts with OH or $NH_2$ can be used. Such cross-linkers include, but are not limited to, glutaraldehyde, hexamethylene diisocyanate, epichlorohydrin, and ethylene glycol diglycidyl ether. However, cross-linking decreases the number of functional groups, and consequently the potential ligand density. The chitosan molecule contains two functional groups, OH and $NH_2$, with the latter being more active than the former. In one preferred embodiment, to maintain the number of amine groups, epichlorohydrin is used since, under basic conditions, it reacts only with the OH groups.

Chitin microporous or macroporous membranes are obtained via acetylation of the corresponding chitosan membranes with acetic anhydride in methanol. The N-acetylated chitosan (chitin) membrane has a stronger chemical resistance than chitosan membrane, being insoluble in 5 vol % aqueous solution of acetic acid (pH 2.5) and in 5 wt % aqueous NaOH solution. This increased chemical resistance is most likely due to the presence of $COCH_3$ group, which decreases the elongation upon increasing the extent of crystallinity.

The method of the present invention can also be employed to prepare composite membranes, in which chitosan is blended with synthetic polymers such as, but not limited to, polyvinyl alcohol (PVA), polyvinyl pyrrolidone (PVP), polyethylene oxide (PEO), poly amides, polyacrylamides, polymethacrylate and polyhydroxyethyl methacrylate, or natural polymers such as, but not limited to, gelatin, collagen, dextran, agarose, silk, cellulose and cellulose derivatives. Such combinations would be useful in improving the properties of polymer membranes, such as blood compatibility, mechanical properties and biodegradability.

The present invention is not limited to flat sheets, but can be used in other forms including, but not limited to, hollow fibers and beads. Flat membranes can be housed in a support assembly. In a preferred embodiment, the support assembly is a plate type filtration cartridge wherein, multiple membranes can be stacked. Stacking of multiple membranes increases the adsorptive capacity of the membranes.

In contrast to most commercial membranes, the membranes of the present invention contain a large number of active groups (—OH and/or $NH_2$). Therefore the membranes of the present invention can be used, without any further amplification of the number of active groups, in various applications such as affinity membranes. Since chitin membranes contain N-acetyl-D-glucosamine units in its structure, it can be used to bind macromolecules that have an affinity for this group. Such macromolecules include, but are not limited to, lysozyme and wheat germ agglutinin.

Chitosan membranes can bind molecules that have an affinity for glucosamine. Such molecules include, but are not limited to, protein A and Cibacron™ Blue F3GA dye. Other potential uses for macroporous and microporous chitosan and chitin membranes include, but are not limited to, agents for wound dressing, hemostatic bandages, metal chelating agents, enzyme carriers, agents for cell immobilization, and blood filters to remove selected cells.

These and other applications will become more clear from the following examples:

EXAMPLE 1
Preparation of Chitosan Macroporous Membranes

Illustrated in this embodiment is the preparation of chitosan membranes. A solution of chitosan was first obtained by dissolving 1 g of chitosan in 100 ml of 1 vol % aqueous acetic acid solution containing 10 wt % glycerol. To this solution, the desired size and amount of silica particles were added, followed by vigorous stirring in order to disperse them uniformly. Then the solution was poured onto a rimmed glass plate and the liquid was allowed to evaporate. The dried membrane was immersed in a 5 wt % aqueous NaOH solution and kept for 2 hours at 80° C. Finally, the porous membrane was washed with distilled water to remove the remaining NaOH.

EXAMPLE 2
Cross-linking of Microporous or Macroporous Chitosan Membranes

While insoluble in alkaline solutions, the chitosan membrane is soluble in dilute acetic acid solutions. To prevent the dissolution of chitosan membrane under acidic conditions, which are necessary to elute many biomolecules, the chitosan membrane must be cross-linked. Cross-linking of the chitosan membrane was carried out under mild conditions using epichlorohydrin as the cross-linker. The chitosan membranes were immersed in $1 \times 10^{-2}$ M epichlorohydrin solution, containing 0.067M NaOH (pH 10) for 2 hours at 50° C. Then the membranes were taken out of the solution and rinsed with distilled water until neutral conditions. Table 1 shows the effect of cross-linking of chitosan membranes.

TABLE 1

| chitosan membrane | in 5 vol % aqueous acetic acid soln, pH 2.5 | flux (ml/min/cm$^2$) at pressure drop of ⅗ psi |
| --- | --- | --- |
| before cross-linking | soluble | 18.1/27.4 |
| after cross-linking | insoluble | 17.3/26.0 |

In order to prevent its shrinkage during drying, the membrane was immersed in a 20 vol % aqueous glycerol solution for 30 min and, after removing the excess glycerol solution, placed on a glass plate and allowed to dry. Thus, a strong and flexible membrane that had not undergone shrinkage, was obtained.

EXAMPLE 3
Conversion of Macroporous Chitosan Membranes to Macroporous Chitin Membranes To prepare chitin membranes, the corresponding chitosan membranes were acetylated after removal of the alkaline solution used to dissolve the porogen particles. The acetylation of chitosan membranes to chitin was carried out via its immersion into a stirred solution of 100 ml methanol containing 5 ml of acetic anhydride for 1 hour at 50° C. The membranes were then removed from the solution and washed successively with methanol and distilled water, followed by treatment of the membrane with 5 wt % aqueous NaOH solution overnight to remove the $CH_2OH$ acetylated groups. Finally, a white macroporous chitin membrane was obtained after washing with distilled water until neutral conditions. Table 2 presents a comparison of the chemical resistance and mechanical properties, and Table 3 presents a comparison of the physical properties of chitin and chitosan membranes. The mechanical properties of the chitosan and chitin membranes were determined at 20° C. using an Instron™ universal testing instrument(Model 1000). The gauge length was 20 mm and the extension rate 10 mm/min. The specific adsorption areas of chitosan and chitin macroporous membranes were determined by the BET (Brunauer-Emmett-Teller) method using a Micromeritics™ ASAP 2000 instrument. The porosities of the chitosan and chitin membranes were obtained by determining their swelling in water and using the following expression:

$$\text{porosity } (\%) = \{(W_1 - W_2)/d_{water}\} 100/V$$

where $W_1$ and $W_2$ are the weights of the membranes in the wet and dry states, respectively, $d_{water}$ is the density of pure water at 20° C., and V is the volume of the membrane in the wet state.

TABLE 2

| membrane | chem resistance in mechanical properties (dry/wet) | | | |
|---|---|---|---|---|
| | 5 wt % NaOH solution | 5 vol % HOAc solution | tensile strength, MPa | elongation at break, % |
| chitosan | insoluble | soluble | 7.37/0.90 | 6.1/102.2 |
| chitin | insoluble | insoluble | 9.23/1.09 | 4.6/29.3 |

TABLE 3

| membrane | thickness, $\mu$m | porosity, % | spec adsorption area m$^2$/g | average pore size $\mu$m | flux (ml/min/cm$^2$) at pressure drop of ⅗ psi |
|---|---|---|---|---|---|
| chitosan | 119 | 75.2 | 1.8 | 19.8 | 17.6/30.8 |
| chitin | 132 | 62.2 | 1.6 | 17.9 | 15.0/28.9 |

EXAMPLE 4

Figure 1B:
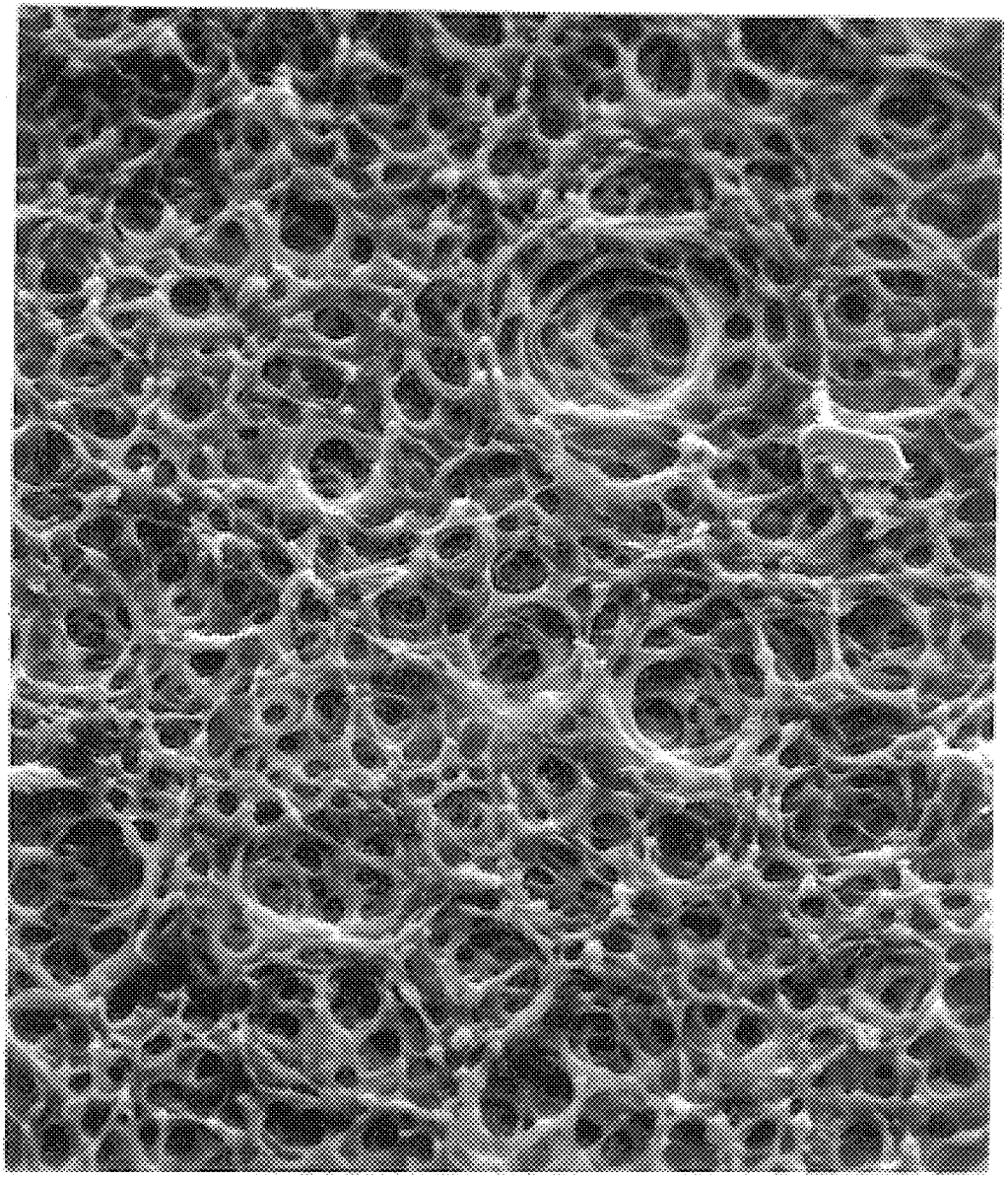
FIG. 1b is a scanning electron micrograph showing the morphology of a macroporous chitosan membranes, wherein the size of silica particles is 10 μm and the weight ratio of silica to chitosan is 4:1.
Figure 1C:
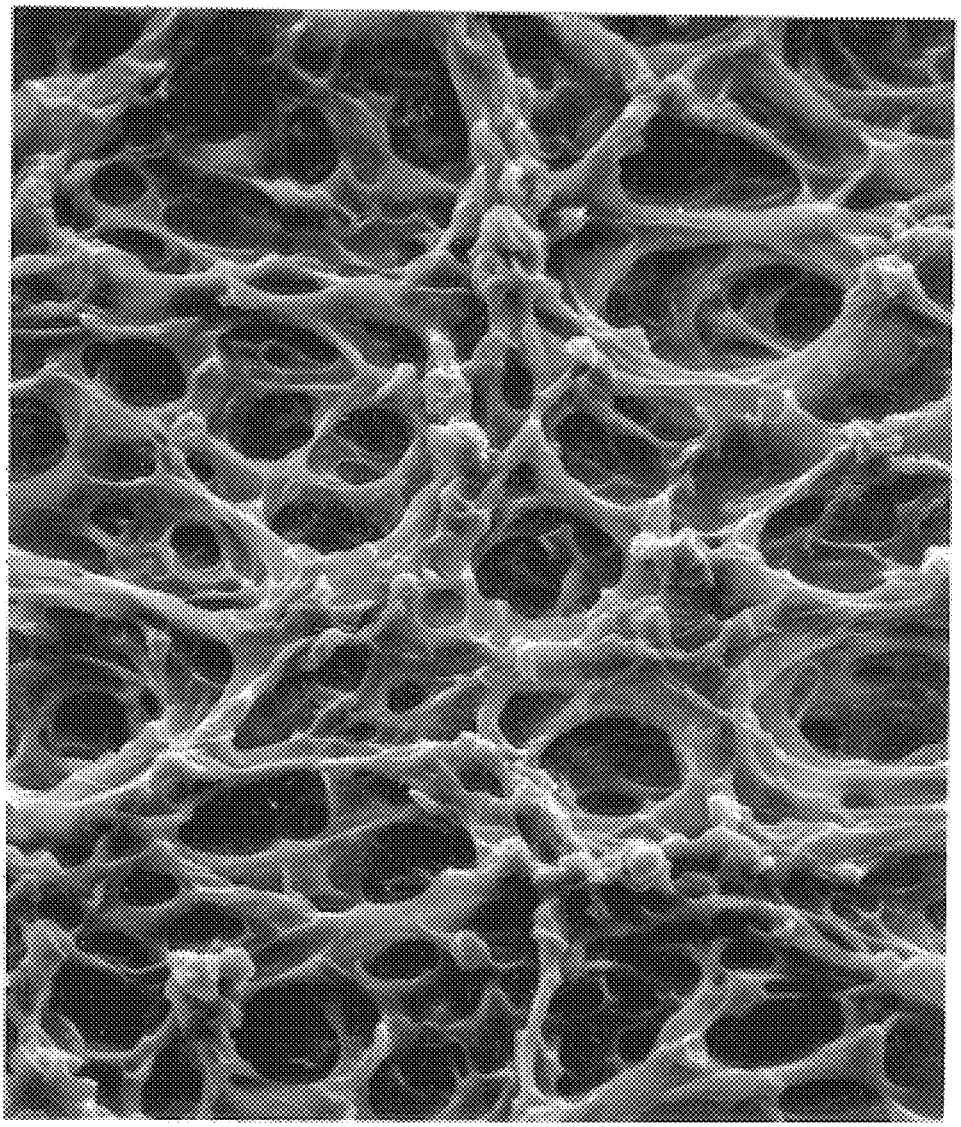
FIG. 1c is a scanning electron micrograph showing the morphology of a macroporous chitosan membranes, wherein the size of silica particles is 15–40 μm and the weight ratio of silica to chitosan is 4:1.

Morphology of Chitosan and Chitin Membranes:

Scanning electron microscopy was employed to investigate the morphology of the chitosan and chitin membranes. The specimen were prepared as follows: the wet membrane was wiped with a filter paper to remove the excess water present on the surface of the membrane, then framed on a petri dish to prevent shrinkage along the surface, and allowed to dry. The membranes were fractured under liquid nitrogen and the fractured surfaces were coated with a thin layer of carbon before scanning. FIGS. 1(a), 1(b) and 1(c) show that the pores are distributed uniformly indicating that the silica particles were dispersed uniformly.

EXAMPLE 5

Figure 2:
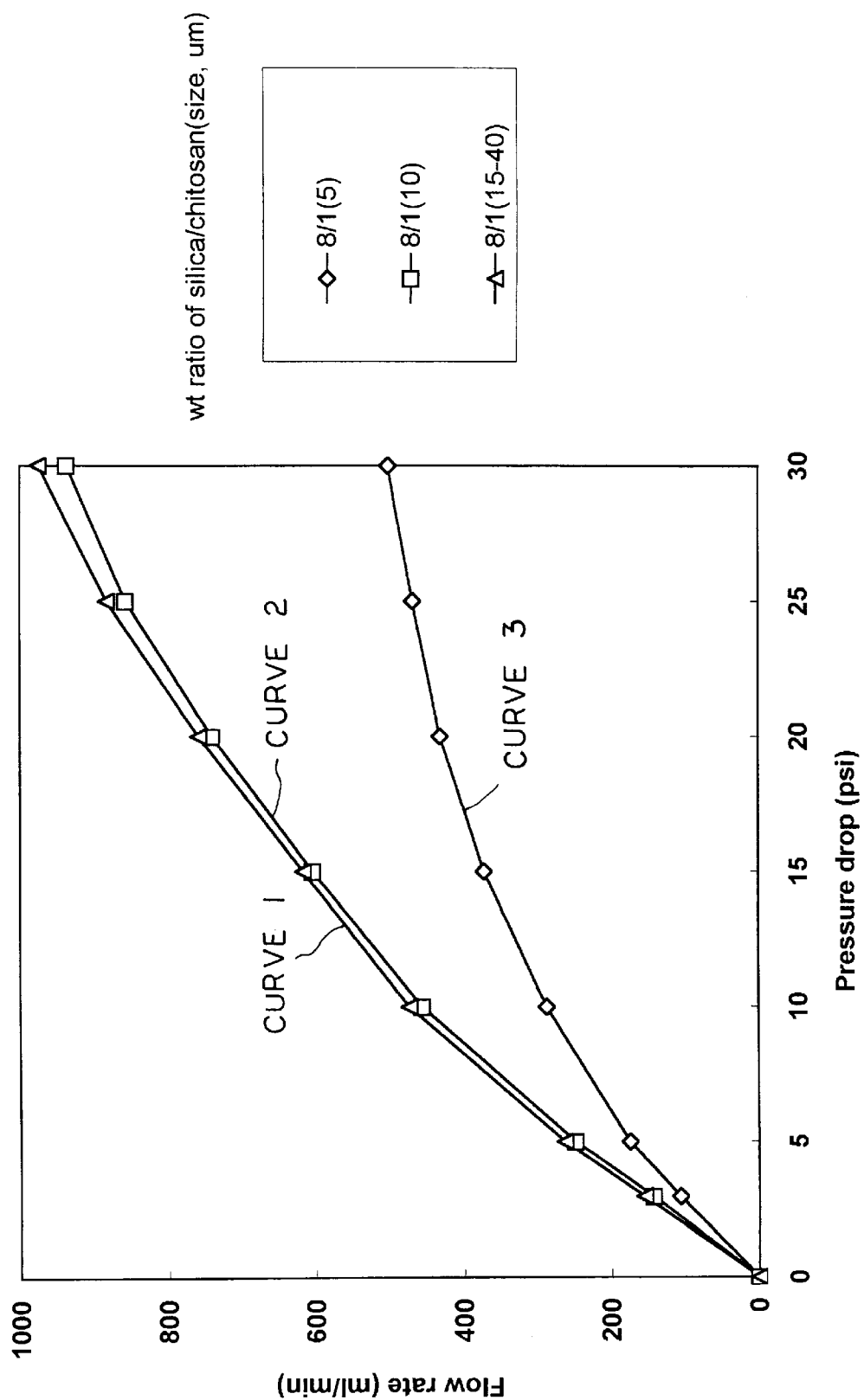
FIG. 2 is a graph illustrating the effect of the size of silica particles on the flow rate through chitosan membranes.

Effect of Size of Silica Particles on the Morphology and Flow Rate through Chitosan Membranes:

To determine the effect of the size of silica particles on the morphology of the membrane and on the rate of flow of fluids through the membrane, three kinds of silica particles, size between 15 and 40 $\mu$m, average size of 10 $\mu$m, and average size of 5 $\mu$m, were selected for illustration. The morphologies of the chitosan membranes can be seen from the electron micrographs of FIG. 1a (5 $\mu$m), FIG. 1b (10 $\mu$m), and FIG. 1c (15–40 $\mu$m), which show three-dimensional networks with high porosities and uniformly distributed pores. A comparison of the flow rates through these membranes is presented in FIG. 2. The flow rate for membranes prepared with silica particles of sizes 15–40 $\mu$m (curve 1) and 10 $\mu$m (curve 2) was higher than that for membranes prepared with silica particles of size 5 $\mu$m (curve 3). The larger silica particles provided the larger pore sizes and, hence, the larger flow rates of pure water through the membrane. The average pore size of membranes prepared with a weight ratio of silica to chitosan of 8:1 and with silica particles of sizes 15–40 $\mu$m, 10 $\mu$m and 5 $\mu$m membranes was 19.5 $\mu$m, 6.6 $\mu$m, and 2.5 $\mu$m respectively. These results indicate that the size of the pores can be controlled by selecting silica particles of appropriate size. In addition, the electron micrographs indicate that the pores are uniformly distributed.

EXAMPLE 6

Preparation of Composite Membranes containing Chitosan and Synthetic Polymers

In one embodiment of the invention, chitosan is blended with synthetic polymers to make composite membranes. Chitosan and PEO were dissolved individually in 1 vol % aqueous acetic acid solution containing 10 wt % glycerol. Then the two solutions were mixed in various proportions. The silica particles (15–40 $\mu$m) were suspended via stirring in the mixture; this was followed by casting the suspension on a rimmed glass plate. After drying at room temperature, the dried membrane was immersed in 5% NaOH solution at 80° C. for 2 hours, followed by washing with distilled water. This produced a macroporous chitosan-poly(ethylene oxide) blend membrane.

To prepare a chitosan-polyvinyl alcohol blend membrane, the casting solution was prepared by mixing a 2 wt % polyvinyl alcohol (PVA) aqueous solution with a 1 wt % chitosan aqueous acetic acid solution containing 10 wt % glycerol and silica particles (15–40 $\mu$m). Dissolution of silica particles was carried out by immersion in 5% NaOH at 60° C. for 5 hours.

EXAMPLE 7

Preparation of Composite Membranes containing Chitosan and Natural Polymers

In one embodiment of the invention, composite membranes containing chitosan and collagen or chitosan and gelatin were prepared. One wt % solutions of chitosan and collagen or gelatin were prepared by dissolving them individually in a 2 vol % aqueous acetic acid solution. The individual solutions were then mixed in a 1:1 volume ratio. Silica particles (15–40 $\mu$m) were added with vigorous mixing, followed by casting the suspension on a rimmed glass plate and drying at room temperature. The dried membrane was immersed in 5% NaOH solution at 60° C. for 5 hours, followed by washing with distilled water.

EXAMPLE 8

Preparation of membrane cartridge

Figure 3:
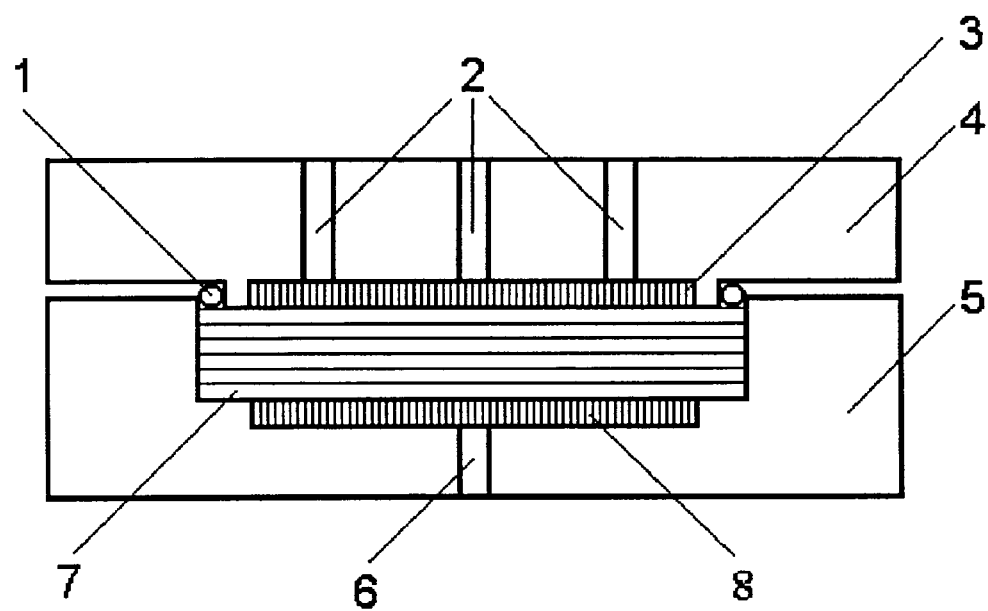
FIG. 3 is a schematic diagram of a cartridge used to house chitosan or chitin membranes for affinity filtration.

In one embodiment of this invention, the membrane is housed in a plate type filtration cartridge. While any cartridge known to those skilled in the art can be used, an example of such a cartridge is presented here. A schematic diagram of the cartridge is presented in FIG. 3. Two porous sintered plates (3 mm thick) were employed as distributors in the cartridge. In addition, multi-inlet ports (4 inlets) and a bubble relief valve were employed in order to achieve better sample distribution. The cartridge has a hollow bottom portion 5, the bottom of which houses a flow collector 8 which leads to an outlet port 6. The stacked chitosan membranes 7 are placed on the flow collector. The top cover of the cartridge 4 has a flow distributor 3 which, together with the flow collector 8, sandwiches the chitosan membranes 7. The flow distributor 3 in the cover 4 has three inlet ports 2 to feed the fluid to the membranes. The purpose of the flow distributor is to feed the fluid uniformly to the membranes. The cover houses an "O"-ring seal 1, which seals the chitosan membranes from the outside.

EXAMPLE 9

Preparation of hollow fibers

In one embodiment of this invention, the membrane is in the form of a hollow fiber. For preparing hollow fibers, an acidic chitosan solution containing silica particles of desired size is placed into a cylinder and extruded with a piston through a spinneret into a coagulation bath (aqueous 5% wt NaOH, which may contain ethanol or methanol). While not intending to be bound by any particular theory, it is believed that this solidifies the fiber by deprotonating the amine group. This is followed by drawing the fiber through a washing bath (deionized water) to remove the sodium hydroxide, and then through an acetone bath to dehydrate the fiber. Glycerine may be added into the spin dope, the coagulating solution and washing bath to prevent rupture during drying. Subsequently the fiber is immersed in a NaOH solution at 80° C. to dissolve the silica particles and to generate the porous fiber. A hollow fiber spinneret can be employed to prepare chitosan hollow fiber. Treatment with a cross-linker, as in Example 2, is needed to stabilize the membranes. Micro- or macroporous chitin fibers or hollow membranes can be prepared by acetylating the chitosan fiber or hollow fiber with acetic anhydride.

EXAMPLE 10

Preparation of beads:

In another embodiment of this invention, chitosan and chitin beads are prepared. To prepare chitosan beads, a suspension of silica particles in acidic chitosan solution is dropped through a nozzle, using compressed air, into a stirred NaOH or NaOH-methanol solution to form chitosan beads. The formed beads are filtered and washed with deionized water and methanol, followed by drying. The silica-containing beads are immersed in a 5 wt % NaOH to dissolve the silica particle, and to generate micro- or macroporous chitosan beads. A cross-linker, for example, glutaraldehyde, hexamethylene diisocyanate or ethylene glycol diglycidyl ether, can be used to harden the beads.

For the preparation of beads, these cross-linkers are preferred over epichlorohydrin since the use of these cross-linkers results in hard beads that are easier to process than the epichlorohydrin treated beads. To prepare chitin beads, the chitosan beads can be treated with acetic anhydride.

EXAMPLE 11

Figure 4:
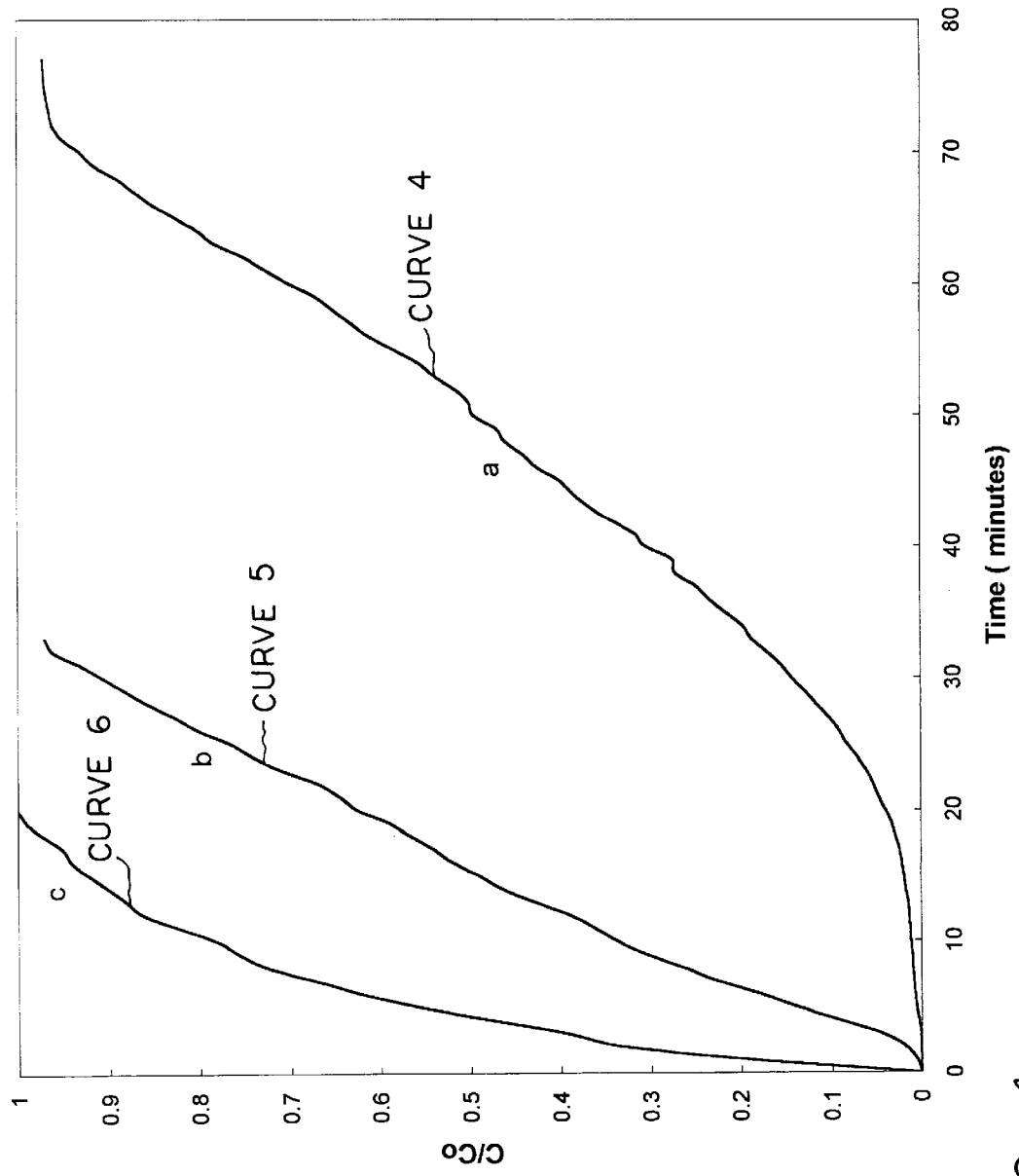
FIG. 4 is a graph illustrating the adsorption of lysozyme on the chitin membrane cartridge at 20° C.
Figure 5:
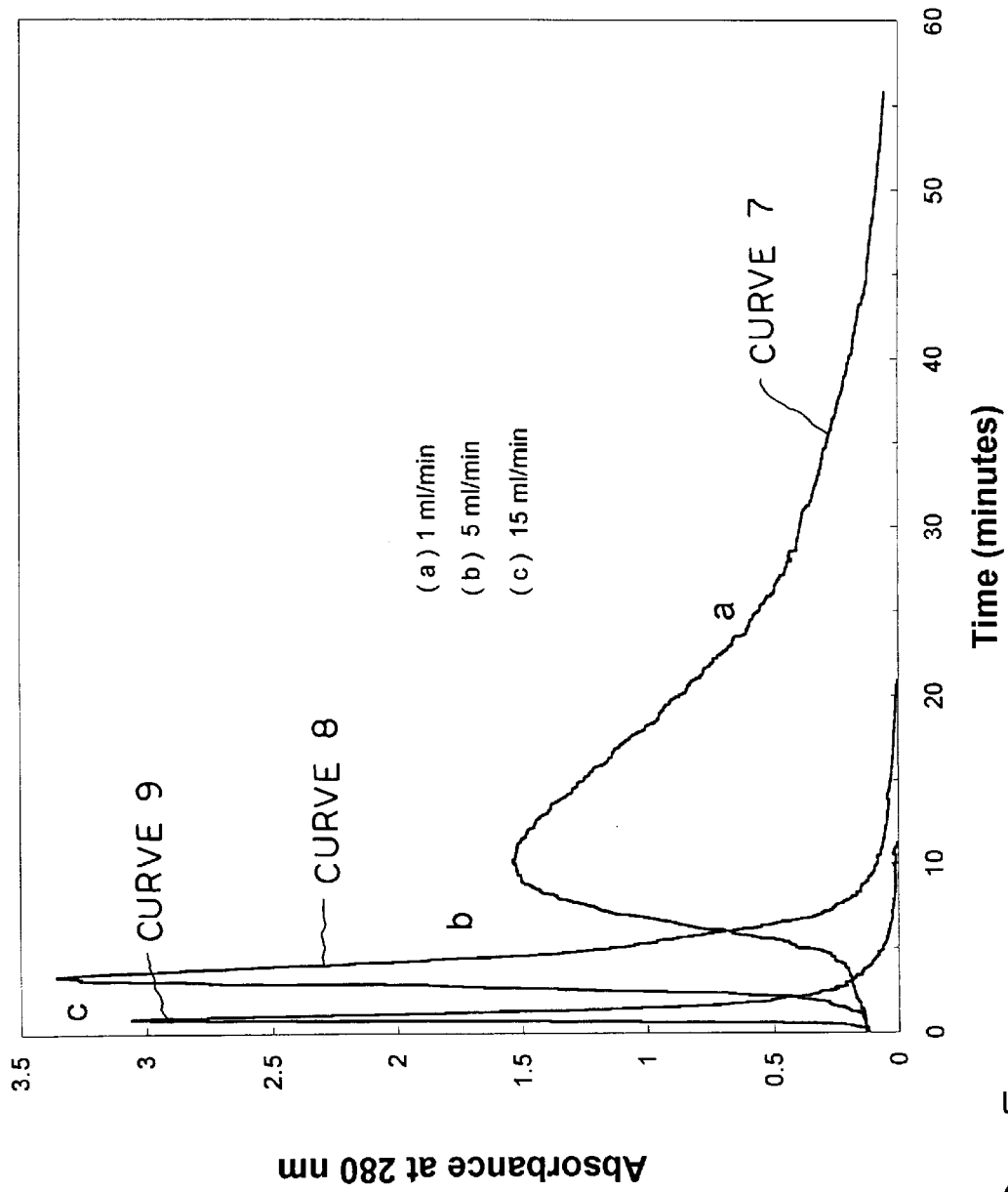
FIG. 5 is a graph illustrating the elution profiles of lysozyme at three different flow rates: (a) 1 ml/min; (b) 5 ml/min; (c) 15 ml/min.

Use of the Membrane:

In one embodiment of the invention, the membrane is used for affinity purification of lysozyme which has a known affinity for the D-glucosamine moieties of chitin. A 1 mg/ml solution of lysozyme in 0.1 M phosphate buffer (pH 8.0) containing 1 M NaCl was prepared and loaded at a flow rate of 1, 5, or 15 ml/min into the chitin cartridge of Example 8. The ratio of the concentration of lysozyme in the effluent (C) and the initial concentration of lysozyme ($C_o$) is plotted as a function of time in FIG. 4. The time required to achieve saturation was about 20 min for 15 ml/min (c; curve 6), about 30 min for 5 ml/min (b; curve 5) and more than 70 min for 1 ml/min (a; curve 4). The adsorption was followed by washing with phosphate buffer for 10 min at a flow rate of 15 ml/min, and by elution with 0.1 M acetic acid solution at 1, 5, and 15 ml/min, until no protein was detected in the effluent. The effluent was collected and the concentration determined spectrophotometrically. The elution profile is presented in FIG. 5. About 40, 10 and 5 minutes were needed for the elution flows of 1 ml/min (a; curve 7), 5 ml/min (b; curve 8), and 15 ml/min (c; curve 9) respectively to remove 95% of the strongly bound protein.

EXAMPLE 12

Use of the Membrane to Purify Lysozyme from Egg White

Figure 6:
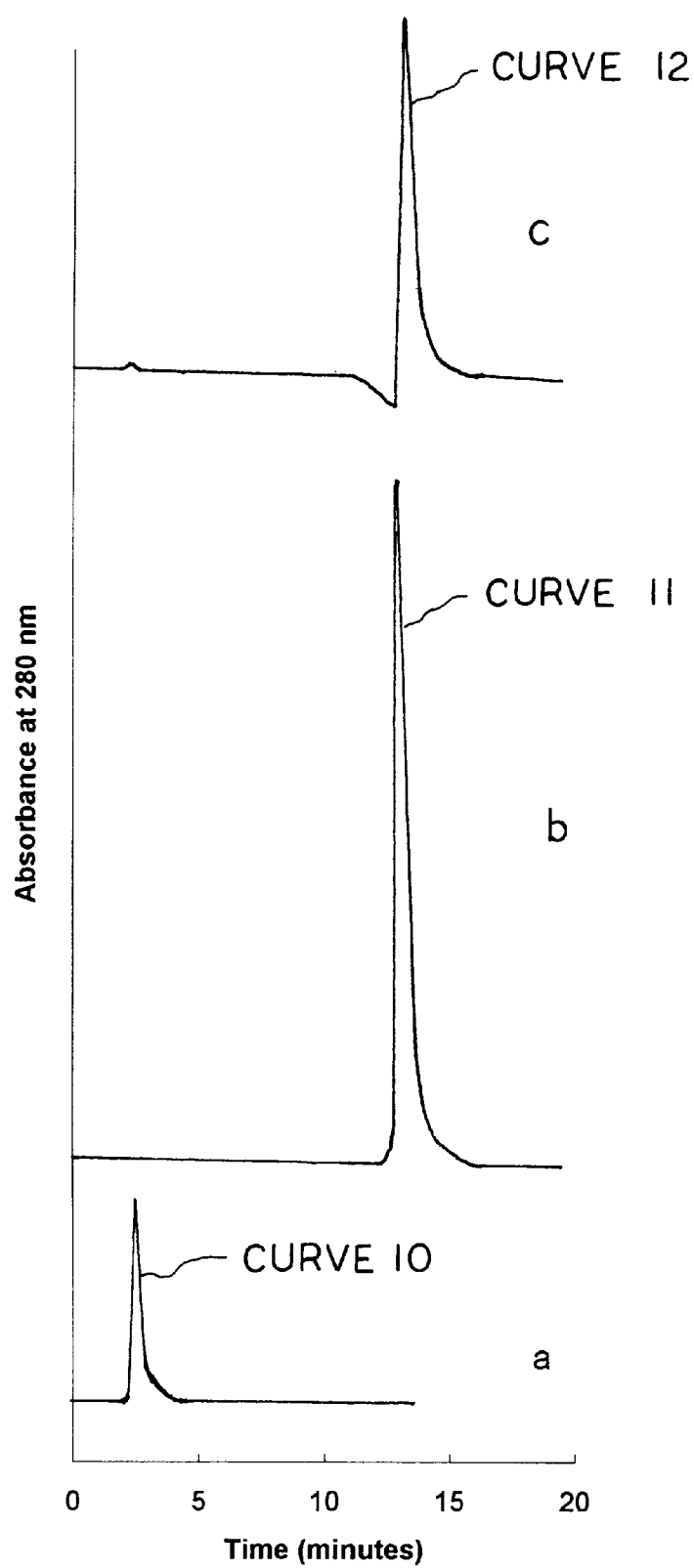
FIG. 6 is a graph illustrating HPLC elution profiles of (a)—pure ovalbumin; (b)—pure lysozyme; and (c)—lysozyme separated from egg white using a chitin cartridge.

In one embodiment of the invention, the membrane was used for separation of lysozyme from egg white. Hen egg white was first separated from fresh eggs. Then 10 ml of homogenized egg white was diluted with 90 ml of 0.1 M phosphate solution (pH 8.0) containing 1 M NaCl, followed by filtration and centrifugation at 100 g for 20 min. Finally, 65 ml of supernatant was pumped through the chitin cartridge of Example 8, at 1 ml/min, followed by 10 min washing at 15 ml/min and about 15 min elution at 5 ml/min. The purity of the lysozyme was examined by High Performance Liquid Chromatography (HPLC) using a wide-pore CBx HPLC column, 5 µm, 7.75 mm×100 mm. The flow rate was 1 ml/min, the mobile phase A binding buffer was 25 mM MES ((2-N-morpholino) ethanesulfonic acid), pH 5.6 and the mobile phase B eluting buffer was 1 M NaOAc, pH 7.0. The sample size was 100 µl. The various profiles in FIG. 6 represent pure ovalbumin (a; curve 10), pure lysozyme (b; curve 11) and lysozyme from egg white (c; curve 12). The purity of lysozyme from egg white was estimated to be higher than 98% and its specific activity was 54,003 units/mg protein.

It is appreciated that various modifications to the inventive concept may be apparent to those skilled in the art without departing from the spirit and scope of the present invention defined by the hereinafter appended claims.

What is claimed is:

1. A membrane selected from the group consisting of a microporous and macroporous membrane, wherein said membrane is composed of a matrix and a set or pores, wherein said matrix consists essentially of chitosan, and wherein said pores are formed by dissolution of a particulate porogen, wherein said pores are uniformly distributed and include a three-dimensional structure.

2. A membrane selected from the group consisting of a microporous membrane and macroporous membrane wherein said membrane is composed of a matrix and a set or pores, wherein said matrix comprises chitosan and at least one polymer selected from the group consisting of polyethylene oxide, polyvinyl alcohol, collagen and gelation, and wherein said pores are uniformly distributed and have a three dimensional structure.

3. The membrane of claim 2, wherein said polymer is polyethylene oxide.

4. The membrane of claim 2, wherein said polymer is polyvinylalcohol.

5. The membrane of claim 2, wherein said polymer is collagen.

6. The membrane of claim 2, wherein said polymer is gelatin.

7. The membrane according to claim 1, wherein said porogen comprises silica particles.

8. The membrane according to claim 7, wherein the membrane is a macroporous membrane, and wherein said silica particles have a diameter of between about 15 µm to about 40 µm.

9. The membrane according to claim, 1 wherein chitosan has a molecular weight of between about 400,000 to about 2,000,000.

10. The membrane according to claim 1 wherein chitosan is N-acetylated.

11. A method for the preparation of a membrane according to claim 10, comprising the steps of:

a. suspending porogen particles in an acidic solution comprising chitosan b. shaping the suspension into a membrane;

c. extracting the porogen by contacting the membrane with an aqueous alkaline solution;

d. removing the alkaline solution; and e. converting chitosan to chitin by treating the membrane with acetic anhydride.

12. The method of claim 11, wherein said porogen comprises silica particles.

13. The method of claim 12, wherein the silica particles have a diameter of between about 15 µm to about 40 µm, wherein chitosan has a molecular weight of between about 400,000 to about 2,000,000, and wherein the porogen is extracted by heating in an alkaline solution comprising sodium hydroxide.

14. The method of claim 11, wherein the porogen is extracted by heating in the aqueous alkaline solution.

15. The method of claim 11, wherein the suspension is shaped into a flat sheet by casting on a flat surface.

16. The method of method of claim 11, wherein the suspension is shaped into hollow fibers by extruding through a spinneret.

17. The method of claim 11, wherein the suspension is shaped into beads by dropping through a nozzle.

18. The method according to claim 11, further comprising the step of treating the membrane with a plasticizer to soften the membrane, after step (e).

19. The method of claim 18, wherein the plasticizer is glycerol.

20. The method of claim 11, wherein the acidic chitosan solution further comprises a plasticizer.

21. The method of claim 20, wherein the plasticizer is glycerol.

22. The membrane according to claim 1, wherein the membrane is in the form of a flat sheet.

23. The membrane according to claim 1, wherein the membrane is in the form of a hollow tube or fiber membrane.

24. The membrane according to claim 1, wherein the membrane is in the form of a bead.

25. A method for the preparation of a membrane according to claim 1, comprising the steps of:

a. suspending porogen particles in an acidic solution comprising chitosan;

b. shaping the suspension into a membrane;

c. extracting the porogen by contacting the membrane with an aqueous alkaline solution;

d. removing the alkaline solution; and e. treating the membrane with a cross-linker.

26. The method of claim 25, wherein said porogen comprises silica particles.

27. The method of claim 26, wherein the silica particles have a diameter of between about 15 µm to about 40 µm, wherein chitosan has a molecular weight of between about 400,000 to about 2,000,000, wherein the porogen is extracted by heating in an alkaline solution comprising sodium hydroxide, and wherein the cross-linker is epichlorohydrin.

28. The method of claim 25, wherein said cross-linker is epichlorohydrin.

29. The method of claim 25, wherein the porogen is extracted by heating in the aqueous alkaline solution.

30. The method of claim 25, wherein the suspension is shaped into a flat sheet by casting on a flat surface.

31. The method of claim 25, wherein the suspension is shaped into hollow fibers by extruding through a spinneret.

32. The method of claim 25, wherein the suspension is shaped into beads by dropping through a nozzle.

33. The method of claim 32, wherein the cross-linker is selected from the group consisting of glutaraldehyde, hexamethylene diisocyanate and ethylene glycol diglycidyl ether.

34. The method according to claim 25, further comprising the step of treating the membrane with a plasticizer to soften the membrane, after step (e).

35. The method of claim 34, wherein the plasticizer is glycerol.

36. The method of claim 25, wherein the acidic chitosan solution further comprises a plasticizer.

37. The method of claim 36, wherein the plasticizer is glycerol.

38. A method for the purification of molecules, wherein the molecules have a known affinity for the membrane according to claim 1, comprising the steps of:

a. contacting the molecules in solution with said membrane;

b. washing the membrane to remove unbound molecules; and c. eluting bound molecules from said membrane with an acidic solution.

39. The method of claim 38, wherein the membrane is housed in a support assembly.

40. The method of claim 39, wherein the support assembly is a plate type filtration cartridge.

* * * * *

UNITED STATES PATENT AND TRADEMARK OFFICE
CERTIFICATE OF CORRECTION

PATENT NO. : 5,993,661
DATED : November 30, 1999
INVENTOR(S) : Eli Ruckenstein Et Al.

It is certified that error appears in the above-indentified patent and that said Letters Patent is hereby corrected as shown below:

Cover page, item [75] - "Zang" should be -- Zeng --.

Column 10, line 30, "or" should be -- of --.

Signed and Sealed this

Twenty-sixth Day of September, 2000

Attest:

Q. TODD DICKINSON

*Attesting Officer*  *Director of Patents and Trademarks*